US005103810A

United States Patent [19]

Chang

[11] Patent Number: 5,103,810

[45] Date of Patent: Apr. 14, 1992

[54] SEXUAL AID

[76] Inventor: Tao-Ping Chang, 5F-23, 70, Fun-Shing Road, Taoyuan, Taiwan

[21] Appl. No.: 706,174

[22] Filed: May 28, 1991

[51] Int. Cl.[5] ............ A61F 5/41

[52] U.S. Cl. ............ 600/39

[58] Field of Search ............ 128/79

[56] References Cited

U.S. PATENT DOCUMENTS

| | | | |
|---|---|---|---|
| 1,216,099 | 2/1917 | Falck | 128/79 |
| 2,378,795 | 6/1945 | Rupe | 128/79 |
| 3,633,572 | 1/1972 | Wiggins | 128/79 |
| 4,429,689 | 2/1984 | Yanong | 128/79 |
| 4,488,541 | 12/1984 | Garcia | 128/79 |
| 4,640,270 | 2/1987 | Chin | 128/79 |
| 4,724,829 | 2/1988 | Knapps | 128/79 |

*Primary Examiner*—Cary E. O'Connor

[57] ABSTRACT

A sexual aid has a tubular body with a connection piece, two bands sewn or adhered to a lower end of the connection piece and a guard sewn to an upper end of the connection piece. For adjustment of the tightness of the device, a waistband adhered to the guard by adhesive tapes defines slots through which pass ends of the two bands. The tubular body has a number of peaks and valleys running along spiral lines which, with a ring element, stimulate the woman in order to make her reach orgasmic phase more quickly. The tubular body is a hollow structure with a hole at the front end to allow sperm to flow therethrough.

3 Claims, 3 Drawing Sheets

SEXUAL AID

BACKGROUND OF THE INVENTION

Sex is an important factor in maintaining a close relationship between husband and wife. Sexual inadequacy is always a main reason of unhappiness. Woman who can't have her demands satisfied may attempt to satisfy herself by masturbation, and an aged man may be unable to satisfy his wife's demands. Though some food supplements can help sexual competency, they might induce undesirable side-effects, or even make the man permanently impotent. In view of these problems, the present invention has been created as a sexual aid to solve the sexual problems between man and woman.

SUMMARY OF THE INVENTION

The present invention provides a sexual aid, in particular such an aid to help a man satisfy a woman and to bring the woman to orgasmic phase more quickly. The sexual aid comprises: a tubular body having a connection piece; a guard attached to the connection piece; two bands sewn or adhered to a lower end of the connection piece; and waistband attached to an upper end of the guard and defining slots for adjustment of the tightness by adjusting positions of the bands passing through the slots in the waistband. The tubular body is designed with a number of peaks and valleys running along spiral lines, and with a ring element to simulate the woman in order to satisfy the woman more quickly. It also has a contact block between the tubular body and the connection piece to stimulate the woman. The tubular body is a hollow structure for holding the man's penis, and has a hole at the front end to allow the flow of sperm therethrough.

DETAILED DESCRIPTION OF THE PREFERRED EMBODIMENT

Figure 1:
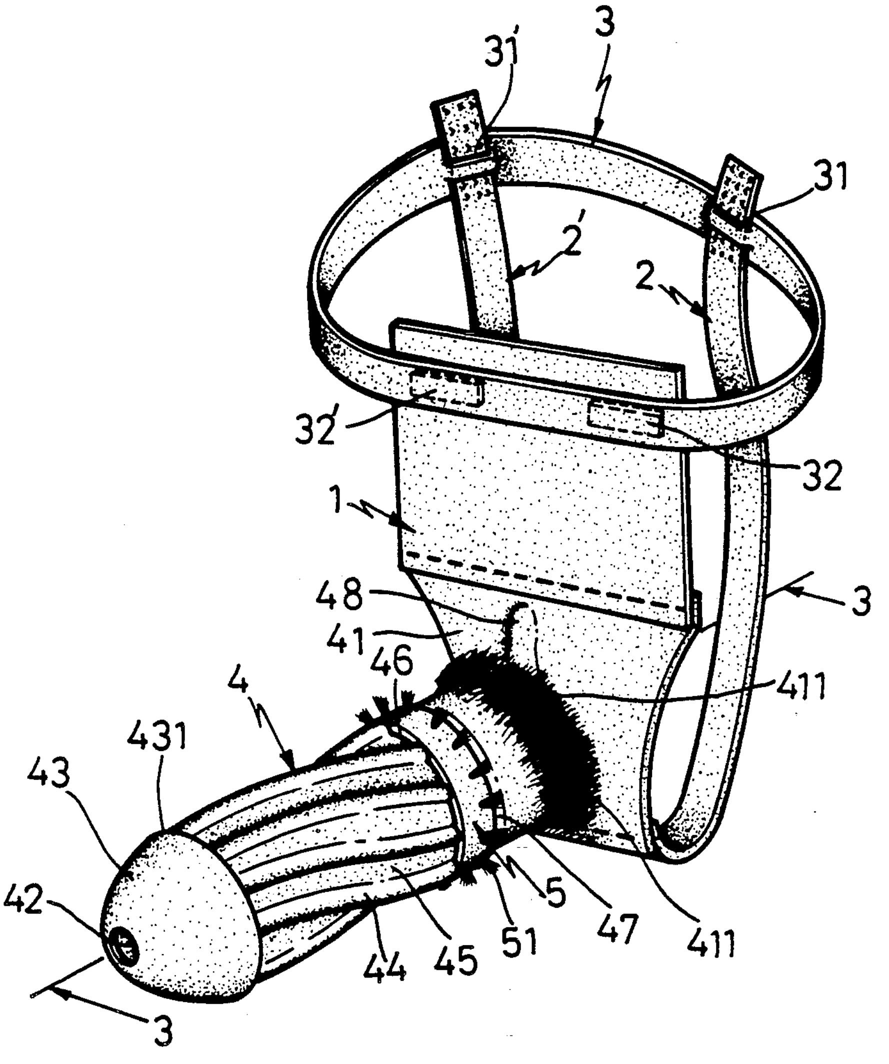
FIG. 1 is a perspective view of a preferred embodiment according to the present invention.

As shown in FIG. 1, the present invention comprises a guard (1), two bands (2 and 2'), a waistband (3), a tubular body (4), and a ring element (5).

Figure 2:
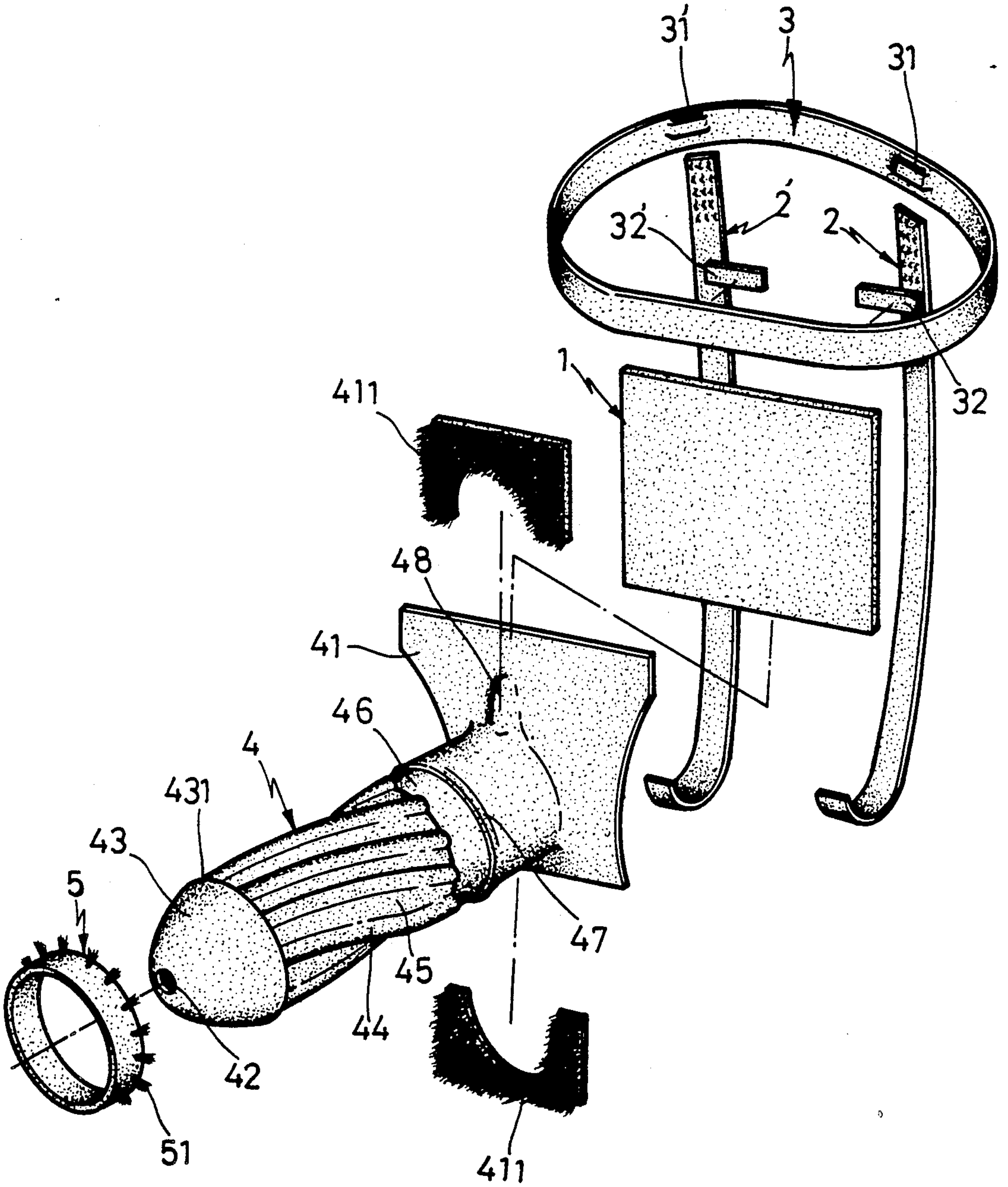
FIG. 2 is an exploded, perspective view of the preferred embodiment according to the present invention.
Figure 3:
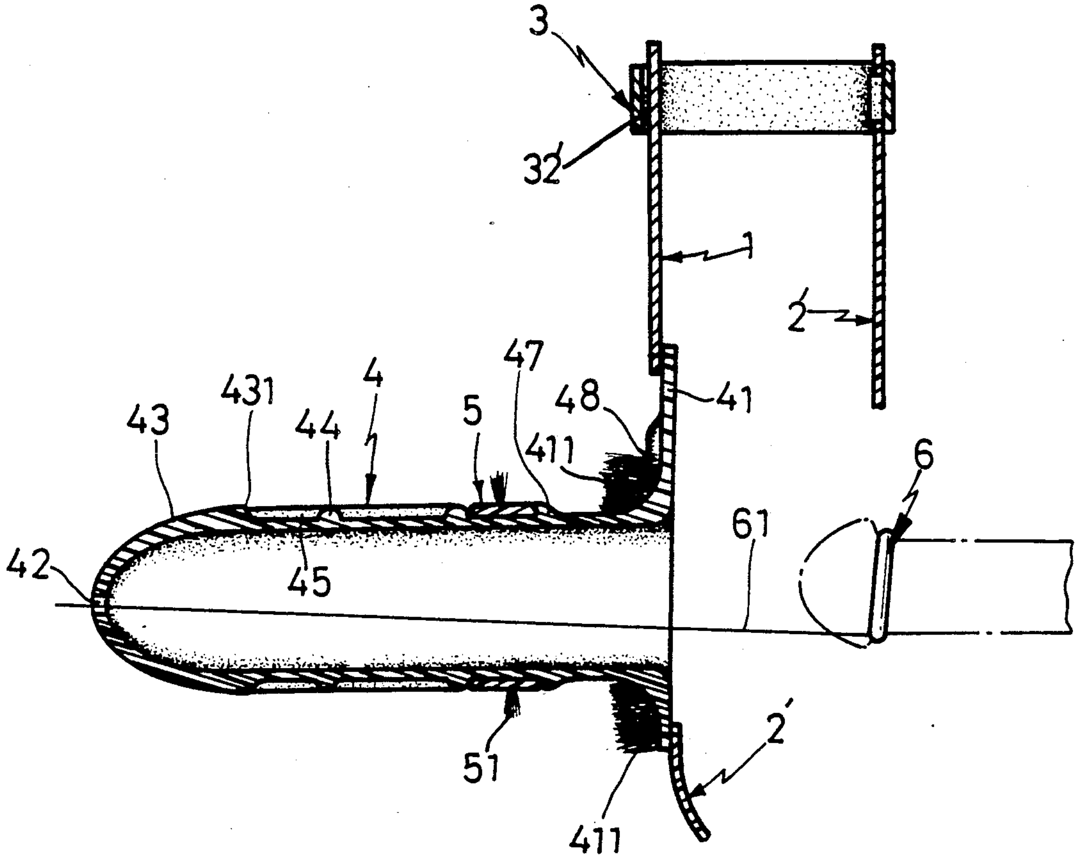
FIG. 3 is a cross sectional view taken along the line 3—3 in FIG. 1.

As shown in FIGS. 1, 2 and 3, the guard (1) is connecting to a connection piece (41) of the tubular body (4) with adhesive or by sewing. The bands (2 and 2') are fixed to the lower end of the connection piece (41) by sewing. After putting on the present invention, the tightness can be adjusted by adjusting the position of bands (2 and 2') extending through two slots (31 and 31') in the waistband (3). The guard (1) is made of any fabric material which can be adhered by the adhesion elements (32 and 32') to the waistband (3) to ease adjustment of its position. At an appropriate position on the connection piece a fur element, having fur (411), such as rabbit fur, is fixed. The tubular body (4) and the connection piece (41) according to the present invention are made of material with suitable softness, such as silicone or natural rubber, so that it can provide a comfortable feeling without any risk of injuring the vagina.

The tubular body (4) is a hollow structure with a hole (42) through the front end (43). The front end (43) is designed with a shape like the man's glans. The intermediate portion of the tubular body (4) has a number of peaks (44) and valleys (45) such that none of the peaks (44) is higher than the highest point (431) of the front end (43) to prevent injury to the vagina. The peaks (44) and the valleys (45) run along appropriate spiral lines to provide a highly exciting effect during love making. The valleys (45) also provide a ventilation effect to prevent an uncomfortable feeling being felt by the woman when making love. A ring groove (46) is designed at an appropriate location on the intermediate portion of the tubular body (4) for fixing a ring element (5). The ring groove (46) has a stop edge (47) to prevent the ring element (5) from unwanted displacement. Soft hairs (51) are secured on the ring element (5) at appropriate intervals to stimulate the woman. A contact block (48) extends on the connection piece (41) above the tubular body (4) to contact the woman's clitoris for enhancing excitation. The design of the ring element (5) and the contact block (48) make the woman reach the orgasmic phase in the shortest time.

As shown in FIG. 3, the present invention is also designed for the man's comfort and convenience. A ring (6) may be attached to the man's glans to help assist in extending his penis into the tubular body (4) by pulling of a wire (61). The hole (42) at the front end of the tubular body (4) is designed to allow sperm to flow therethrough.

I claim:

1. A sexual aid comprising:

a) a hollow tubular body, adapted to receive a penis, having a proximal end, a distal end, and an intermediate portion extending between said ends, said body made of a soft material in the shape of a penis, said distal end being in the shape of a glans and having a hole therein, said intermediate portion having a plurality of peaks and valleys extending lengthwise of the body and running along parallel lines;

b) stop means comprising a ring groove having a stop edge on said intermediate portion;

c) a connection piece connected to the proximal end of said body;

d) a contact block protruding from the connection piece;

e) a piece of fur fixed to the connection piece;

f) a guard made of fabric connected, at its lower end, to the upper end of the connection piece;

g) two bands sewn at their lower ends in the connection piece;

h) a waistband having adhesive means for connection to the guard and having slots to adjustably accommodate said bands, said bands being adjusted by moving said bands through said slots; and i) a ring made of an elastic material having soft hairs located at intervals around the ring, the ring being located in said ring groove; wherein the aid is worn on the penis and used during intercourse, the peaks and the ring stimulate the female to aid in achieving a climax.

2. The sexual aid as claimed in claim 1 wherein none of the peaks are higher than the highest point of the distal end so as to stimulate the female and to prevent injury to the vagina.

3. The sexual aid as claimed in claim 1 wherein said body is made of a material selected from the group consisting of silicone and rubber.

* * * * *